United States Patent [19]

Chang et al.

[11] Patent Number: 4,533,764

[45] Date of Patent: Aug. 6, 1985

[54] PURIFICATION OF BISPHENOLS BY REMOVING RESIDUAL SOLVENT

[75] Inventors: Feng-Chih Chang; David E. Busby; Susan A. Wernli, all of Lake Jackson, Tex.

[73] Assignee: The Dow Chemical Company, Midland, Mich.

[21] Appl. No.: 594,963

[22] Filed: Mar. 29, 1984

[51] Int. Cl.$^3$ ............................................. C07C 37/84
[52] U.S. Cl. .................................... 568/724; 568/748; 568/749
[58] Field of Search ..................... 568/724, 749, 748

[56] References Cited

U.S. PATENT DOCUMENTS

| | | | |
|---|---|---|---|
| 2,791,616 | 5/1957 | Lutene | 568/724 |
| 3,290,390 | 12/1966 | Prahl et al. | 568/724 |
| 3,290,391 | 12/1966 | Prahl et al. | 568/724 |
| 3,673,262 | 6/1972 | Prahl et al. | 568/724 |
| 4,212,997 | 7/1980 | Adams et al. | 568/724 |
| 4,242,527 | 12/1980 | Mark et al. | 568/724 |
| 4,354,046 | 10/1982 | Ladewig et al. | 568/724 |
| 4,408,087 | 10/1983 | Li | 568/724 |
| 4,414,422 | 11/1983 | Ash et al. | 568/724 |
| 4,461,915 | 7/1984 | Mendiratta et al. | 568/724 |

*Primary Examiner*—Werren B. Lone
*Attorney, Agent, or Firm*—A. Cooper Ancona

[57] ABSTRACT

Occluded organic solvent is removed from bisphenol crystals by placing in water maintained at a temperature sufficient to form a molten water-bisphenol phase, holding at that temperature for a time sufficient to transfer the organic solvent to the water phase, flash distilling the organic solvent, cooling molten water-bisphenol phase to produce crystallization and thereafter recovering the bisphenol.

7 Claims, No Drawings

PURIFICATION OF BISPHENOLS BY REMOVING RESIDUAL SOLVENT

BACKGROUND OF THE INVENTION

Bisphenols obtained from the condensation reaction of ketones and phenols are valuable compounds useful in preparation of epoxy resins and polycarbonates. High quality epoxy resins and especially polycarbonates, which in optical applications must have high clarity, require especially pure bisphenols in their preparation.

There are many patents related to the purification of bisphenol; and the extent of the purification necessary is dependent on yield, crude bisphenol purity, and quality of final product desired. One method suggested is the formation of a 1:1 crystalline complex with phenol (U.S. Pat. No. 2,791,616). The phenol complex may be refined by washing with phenol, after which it is remelted and heated under vacuum to decompose the complex and distill out the phenol.

A number of suggested processes describe merely leaching crude bisphenol with a solvent or mixture of solvents selected to dissolve maximum amounts of by-products and minimum amounts of bisphenol. However, the bisphenol obtained from such solvent leaching normally is not pure enough for polycarbonate production. The bisphenol can also be purified by a combination of vacuum distillation and solvent leaching techniques (U.S. Pat. Nos. 3,219,549 and 3,290,391). More complicated, but more effective methods involve crystallization from an organic solvent at a temperature and pressure above the atmospheric boiling point of the solvent (U.S. Pat. No. 3,673,262). In yet another process for purification of bisphenols, a mixture of the reaction product, water and a water immiscible organic solvent is heated to a temperature below the boiling point of the organic solvent to provide two liquid phases which are then cooled to crystal bisphenol (U.S. Pat. No. 3,535,389). U.S. Pat. No. 3,326,986 employs a similar process in which the crude bisphenol is heated and melted in water without any organic solvent. The melt is agitated, then cooled and the crystals washed with a chlorinated organic solvent, e.g., methylene chloride, to remove the impurities.

Another more recent patent (U.S. Pat. No. 4,354,046) employs a crystallization in the presence of water and an organic solvent plus a treatment of the mother liquor with a cation exchange resin and recycling the product to the crystallization step.

Bisphenol produced from solvent crystallization always has some occluded solvent. Such occluded solvent can only be removed by remelting the crystals and destroying the lattice. Vacuum drying of the crystals at temperatures below their melting point fails to remove the occluded solvent. Vacuum distillation at elevated temperatures is a common method of purifying bisphenol A, but requires special equipment and care to exclude air to as not to cause color formation and product degradation. The present invention is directed to a method for removing the remaining small quantities of solvent to a parts-per-million level.

SUMMARY OF THE INVENTION

An occluded organic solvent is removed from bisphenol crystals by placing the crystals in water maintained at a temperature above the solvent or water-solvent azeatrope boiling point and allowing them to melt. The solvent or solvent-water azeotrope is then flash distilled from the aqueous phase, after which the molten bisphenol is crystallized in the presence of water, washed and dried. The product contains less than 10 ppm organic solvent and the product purity is further improved.

DETAILED DESCRIPTION OF THE INVENTION

The process of this invention can be applied to bisphenol crystals which contain any of a number of solvents including: water miscible and/or non-azeotrope forming solvents such as methanol, acetone and methyl formate; and those which do form azeotropes with water such as benzene, toluene, xylene, 2-propanol, chloroform, methylene chloride, ethylene dichloride and trichloroethane.

Crystals of the bisphenol are placed into water maintained at a temperature of about 100° C. or above. Because of the water present a bisphenol-water phase forms and this becomes molten at a temperature much lower than that of the bisphenol itself. This phase separates from the remaining excess water and the solvent occluded by the bisphenol crystals can diffuse into the water phase from whence it can be flash distilled. After this flash distillation the temperature of the bisphenol-water phase is reduced to allow the bisphenol to separate from the water and to crystallize. Alternatively, after the flash distillation the molten phase of bisphenol-water may be put through a stripping column to remove water and the bisphenol recovered as a prill or flake.

While the following examples employ bisphenol A (p,p'-isopropylidene diphenol) and toluene solvent, other bisphenols and the other solvents enumerated above can be employed.

EXAMPLE 1 (Toluene - Water Flash of Wet Bisphenol A Crystals)

A 180 gm-sample of bisphenol A (0.21% o,p', 15% toluene) prepared by toluene crystallization, that had been washed and filtered but not dried, was mixed with 720 gm of water. This mixture was heated at one atmosphere pressure to 100° C. and held for 25 minutes. The toluene-water azeotrope was taken overhead through a condenser. The toluene-reduced bis-water melt was then cooled to 87° C. to effect crystallization and filtered and washed with hot water. The final dried product contains 0.04% o,p' and 6 ppm toluene.

EXAMPLE 2 (Toluene - Water Flash of Dry Bisphenol A Crystals)

An 87 gm-sample of bisphenol A (0.18% o,p', 0.5% toluene) prepared from toluene recrystallization of crude bisphenol was mixed with 300 gm of water. This mixture was heated to 100° C. and held for approximately 25 minutes. The toluene-water azeotrope was taken overhead through a condenser. The essentially toluene free bis-water melt was cooled to 93.0° C. to effect crystallization, filtered and washed with 225 gm of hot water. The final dried product contains 0.04% o,p' and 1 ppm toluene. This process has a 98% yield based on p,p' bisphenol.

The above process requires no high temperatures which can degrade the product. Advantage is taken of the relatively low melting point of the water-bisphenol phase and no melting of the pure bisphenol crystal is required with potential degradation at temperatures above 150° C. Another advantage is further purification of the product through water recrystallization. Either dry bisphenol crystals or solvent-wet crystals from an initial crystallization can be used as feed to the process. In either case a low solvent containing product, i.e. less than 10 ppm, is obtained.

Depending upon whether pressure is employed for the distillation, temperatures up to about 200° C. can be used. Temperatures below that at which a water-bisphenol melt occurs cannot be employed. In the case of bisphenol A this temperature is about 98° C.

Pressure can be employed from atmospheric up to about 200 psi, but atmospheric is preferred.

A weight ratio of bisphenol/water of between about 1/20 and 20/1 is satisfactory to operate the process, but preferred ratios are from about 1/1 to 1/5.

The process of the present invention, which obtains a bisphenol product containing less than 10 ppm organic solvent, consists of the steps of (1) adding bisphenol crystals containing organic solvent to water maintained at a temperature which will produce a water-bisphenol molten phase, (2) maintaining that temperature for a period of time sufficient to permit the organic solvent to transfer to the water, (3) flash distilling substantially all of the organic solvent away from the water, (4) cooling the molten bisphenol-water phase to a temperature which will cause crystallization of the bisphenol, (5) separating the bisphenol crystals from the water and drying them.

We claim:

1. A process for purifying a bisphenol to remove small amounts of organic solvent remaining from a crystallization which comprises (a) adding bisphenol crystals containing said solvent to water maintained at a temperature which will produce a water-bisphenol molten phase, (b) maintaining that temperature for a period of time sufficient to permit the organic solvent to transfer to said water, (c) flash distilling substantially all of said solvent away from said water, (d) cooling said molten bisphenol-water phase to precipitate the crystalline bisphenol, and (e) separating said crystalline bisphenol from said water and (f) drying said crystalline bisphenol.

2. The process of claim 1 wherein the bisphenol is p,p'-isopropylidene diphenol.

3. The process of claim 2 wherein the temperature of the water in step (a) is about 100° C.

4. The process of claim 3 wherein the time in step (b) is at least about one minute.

5. The process of claim 4 wherein the time in step (b) is from about 5 to about 50 minutes.

6. The process of claim 5 wherein the pressure is maintained at about atmospheric.

7. A process for purifying a bisphenol to remove small amounts of organic solvent remaining from a crystallization which comprises (a) adding bisphenol crystals containing said solvent to water maintained at a temperature which will produce a water-bisphenol molten phase, (b) maintaining that temperature for a period of time sufficient to permit the organic solvent to transfer to said water, (c) flash distilling substantially all of said solvent away from said water, (d) stripping said water from said molten water-bisphenol phase, (e) separating solid bisphenol as a prill or flake and (f) drying said prill or flake.

* * * * *